United States Patent [19]

Cohen et al.

[11] Patent Number: 4,667,149
[45] Date of Patent: May 19, 1987

[54] PRECISION NONDESTRUCTIVE TESTING OF METALS

[75] Inventors: Richard L. Cohen, Berkeley Heights; Kenneth W. West, Mendham Township, Morris County, both of N.J.

[73] Assignee: American Telephone and Telegraph Company, AT&T Bell Laboratories, Murray Hill, N.J.

[21] Appl. No.: 499,554

[22] Filed: May 31, 1983

[51] Int. Cl.[4] ............................................. G01R 27/14
[52] U.S. Cl. .......................................... 324/64; 324/62
[58] Field of Search ...................................... 324/64, 62

[56] References Cited

U.S. PATENT DOCUMENTS

| | | | |
|---|---|---|---|
| 3,365,663 | 1/1968 | Yamaguchi | 324/64 |
| 3,474,330 | 10/1969 | Dauphinee | 324/30 |
| 3,665,302 | 5/1972 | Lees et al. | 324/64 |
| 4,503,392 | 3/1985 | Fastrisky et al. | 324/232 |
| 4,503,710 | 3/1985 | Oertle et al. | 73/763 |

FOREIGN PATENT DOCUMENTS

| | | |
|---|---|---|
| 0030889 | 6/1981 | European Pat. Off. |
| 7324882 | 7/1973 | Fed. Rep. of Germany |
| 2600684 | 1/1976 | Fed. Rep. of Germany |
| 2377036 | 9/1978 | France ................ 324/64 |

OTHER PUBLICATIONS

Hinsley, Non-Destructive Testing, 1959, pp. 336-339.
Hallenback et al, Precision Four-Point Probe Resistivity Instrumentation, 1969, p. 736.
Cohen et al, Erratic Welding in Low-Carbon Steels, 2-1981.
Smits, Measurement of Sheet Resistivities with LHC Four-Point Probe, 10-1957, pp. 711-718.
Swartzendruber, Correction Factor Tables for Four-Point Probe Resistivity Measurements on Thin, Circular Semiconductor Samples, 4-1964, pp. 1-7.
Halliday et al, The D.C. Electrical Potential Method for Crack Length Measurement, pp. 85-112.
Uhlir, The Potentials of Infinite Systems of Sources and Numerical Solutions of Problems in Semiconductor Engineering, 8-1954, pp. 105-128.
Kohl, Handbook of Materials and Techniques for Vacuum Devices, 1967, p. 198.
Logan, An A.C. Bridge for Semiconductor Resistivity Measurements Using a Four-Point Probe, 9-1960, pp. 885-919.
Rossiter, An Instrument for Measuring the Resistivity of Metals and Metallic Alloys, Journal of Physics E:-Scientific Instruments, vol. 3, No. 7, Jul. 1970, pp. 530-532.
"Electrical Resistance Probe Method for Inservice Inspection", *Nuclear Power Education Seminar, Chugoku X-Ray Co., Ltd.*, Tsutomu Fujimura, The Headquarters of Engineering Services.
"An Apparatus for Four-Probe Specific Resistance Measurement on Epitaxial Silicon Films", *Measurement Techniques*, vol. 17, No. 11, V. V. Batavin et al, 1974, pp. 1753-1754.
Weast, Handbook of Chemistry and Physics, 51st edition, pp. E126-E128.

Primary Examiner—Reinhard J. Eisenzopf
Assistant Examiner—Jack B. Harvey
Attorney, Agent, or Firm—James H. Fox

[57] ABSTRACT

A large number of applications exists for measuring the resistivity or other properties of ferrous and nonferrous metals, including matching alloys to ensure weld compatibility and measuring weld size to estimate weld strength. In the present invention, a DC current-reversal technique allows for accurate electrical measurement with a 4-point probe, alleviating problems due to surface potentials, thermal effects, and eddy currents that previously rendered such measurements inaccurate. Estimates of thermal conductivity, flaw size and location, among others, can also be obtained.

21 Claims, 14 Drawing Figures

PRECISION NONDESTRUCTIVE TESTING OF METALS

BACKGROUND OF THE INVENTION

1. Field of the Invention

The present invention relates to a method and apparatus for the electrical nondestructive testing of metals.

2. Description of the Prior Art

The electrical resistivity of metals and alloys has been extensively studied. Resistivity measurements have been widely used as a research tool for characterizing phase transitions. In addition, the present inventors have discovered that electrical resistivity changes can be a source of erratic weld penetration in electrical spot welding; see R. L. Cohen and K. W. West, *Tooling and Production*, page 94 (February 1981). Thus, production line control applications can benefit from a quick and easy technique to determine the resistivity of a metal. Similarly, incoming material certification and stockroom sorting procedures would benefit from a quick and easy means of determining resistivity. It is, however, notoriously difficult to make good electrical contact to commercial steels: the surfaces are frequently rough, covered with corrosion spots, oiled, and sometimes passivated, painted, or plated. This has made direct measurement of resistivity by contact techniques impractical. The traditional approach to measuring resistivity is to cut a test sample of small, well-controlled cross section and make a precise measurement of the voltage drop along the sample with a precisely known current. However, it is apparent that this destructive technique is impractical for real-time measurement along a production line, and inconvenient for other applications, including acceptance testing or sorting.

Instruments using eddy current techniques have been widely used for determining the electrical resistivity of aluminum and nonmagnetic stainless steels. These measurements have been used for flaw and microcrack detection and for alloy certification; that is, as a simple way to determine which alloy a particular sheet is made of. The simplicity of the eddy current technique, due to the fact that no electrical contacts are made to the sample, no specially shaped samples need to be cut, with access being required only to one side, and the fact that the instrumentation can be portable and battery operated, contributes to the broad application of this approach. Eddy current measurements have also been extended to study semiconductor materials. However, the eddy current measurement requires significant effort in calibration to account for variations in material geometry which influence the eddy currents measured. In addition, for steels and other alloys of significant magnetic permeability (e.g., $\mu > 1.05$), eddy current determinations need substantial corrections to account for permeability variations, and are thus of limited utility. Thus, electrical resistivity measurements have not been widely used in ferrous metallurgy.

However, as noted above, there are many possible applications of a resistivity measurement, especially in view of the locally inhomogeneous composition of many steel products as a result of segregation of the alloying ingredients during solidification of the ingot. It is desirable that the technique be easily applied, with a minimum of sample preparation and a minimum of instrument calibration. It is especially desirable that it be fast, of high enough accuracy to allow distinguishing alloy compositions, and useful for a wide range of sample sizes.

SUMMARY OF THE INVENTION

We have invented a method and apparatus for testing a metal article having a volume resistivity of less than 200 microhm-cm. This technique comprises contacting the article with at least four spaced probes. A current is initially applied through two of the probes so as to flow in one direction therebetween, while a voltage measurement is taken across another two of the probes. The voltage measured is integrated substantially over the time period of the current application. The current is then reversed in direction, and the aforesaid voltage again measured and integrated. The magnitudes of the integrated voltage measurements are combined. The current reversal is typically accomplished once, but can be accomplished a multiplicity of times. The duration of the one or more current flows in each direction is chosen to provide for an equal amount of charge flow in each direction. By providing a calibration factor to account for the geometry of the metal article and the probe spacing, a direct resistivity readout can be obtained. A weld between two or more pieces of metal can be measured by this technique to give an indication of weld strength. Thermal conductivity, flaw size, and other properties related to the integrated voltage can be determined. Both magnetic and nonmagnetic metals can be tested.

DETAILED DESCRIPTION

The following detailed description relates to a technique for determining the resistivity of a metal, or other property that can be determined by the flow of electrical current therein. As used herein, the term "metal" includes metallic elements, alloys, and mixtures having a volume resistivity of less than 200 microhm-cm. The term "magnetic metal" means a metal having a magnetic permeability of greater than 1.05. The present inventive apparatus and technique relate to our discovery that prior art 4-point probe measurements on metals have typically been substantially limited in accuracy by surface potentials, thermal potentials, and other factors resulting from rust, corrosion, oil, paint, and other contaminants frequently present on the surface of such metals. The present technique substantially reduces the effects of the surface conditions, while at the same time substantially avoiding problems relating to eddy currents that have limited other prior art resistivity techniques, especially in magnetic metals. In addition, by substantially reducing the above-noted surface effects, relatively smaller currents can be used to make the measurement, providing for less heating of a sample, and correspondingly smaller temperature-induced inaccuracies. The present technique provides for ease of use and rapid calibration. In addition, the technique can provide sufficiently high accuracy, with a sufficiently low current flow through the sample under test, that a portable battery-operated instrument becomes feasible. The test is sufficiently rapid with most metals that a production line resistivity measurement becomes feasible. Other advantages and uses of the present technique and apparatus will become apparent.

The 4-point probe (see FIG. 1) is a time-honored method of measuring the resistivity of materials to which good electrical contacts cannot be applied easily. It is widely used in semiconductor characterization. Since the current passes through one set of probes, and the IR voltage drop is detected across another set of probes, the large voltage drop which occurs at the tips of the current probes (10, 11) does not appear at the potential probes (12, 13). The current (I) is typically applied through the outer probes and the voltage (V) measured across the inner probes, as shown. However, reciprocity considerations show that this arrangement can be reversed. The voltage and current probes can also be alternated in the sequence. For convenience in calibrating the measurement, the probe spacings are typically equal (referred to as s herein), but unequal spacings are also possible, with all such variations included herein.

Figure 1:
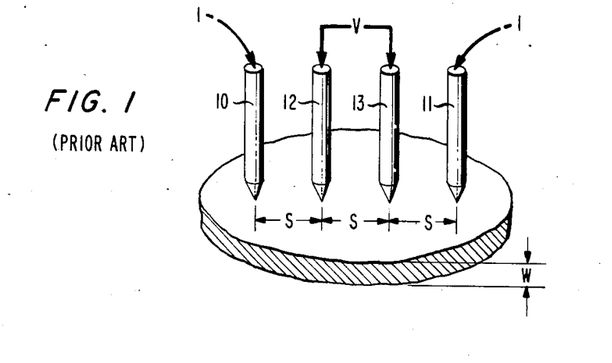
FIG. 1 shows a 4-point probe resistivity measuring technique.

The relationship between resistivity and probe spacing for an infinite sheet for the geometry shown in FIG. 1 has been determined by Smits as $$\rho = \frac{V w \pi}{I \ln 2} F(w/s) \quad (1)$$

where $\rho$ is the resistivity in ohm-cm, V is the voltage across the voltage probes, I is the current through the current probes, and s and w are the probe spacing and sheet thickness in centimeters; see "Measurement of Sheet Resistivities With the Four-Point Probe," F. M. Smits, *The Bell System Technical Journal*, Vol. 37, pages 711–718 (1958). The correction factor F provides for different probe spacings and sample geometries; for w/s less than about 0.5, F is greater than 0.997 and can be considered to be unity. Note that the calibration equation is independent of the probe spacing s for thin samples. Corrections for noninfinite sheets and correction factors (F) for sheets whose w/s is greater than 0.5 have been given by Smits; an extensive numerical table of correction factors is given by L. J. Swartzendruber in *U.S. National Bureau of Standards*, Technical Note No. 199 (1964). In general, if the distance to the nearest edge of the sample is greater than three times the distance between the outermost probes, the error from edge effects is less than 1%. These two considerations indicate the minimum sample diameter and maximum thickness that can be measured with a given probe geometry without correction factors. These corrections can be implemented in the instrument using, for example, analog or digital computational techniques. For measuring samples having large thicknesses and other dimensions large relative to probe spacing, the appropriate "block mode" formula is $$\rho = 2\pi s \frac{V}{I}. \quad (2)$$

The 4-point probe eliminates the effects of contact resistance from the measurement. However, prior art 4-point probe measurements on metals are typically limited by the effects of thermoelectric potentials and electrochemical potentials from surface layers. For example, for currents of about 2 amperes, for s about 1 cm, and for steel of 1 mm thickness, the voltage across the potential probes is only about 200 microvolts. Thus, to make a 1% measurement of the resistivity, the voltage drop must therefore be free of stray potentials to within about 2 microvolts. Such a small tray potential is difficult to reach even with very clean contacts in a laboratory environment.

The present inventive technique provides for making successive measurements with current flowing in opposite directions, integrating the voltages produced thereby, and combining the magnitude of the resulting potentials. Thus, voltages which are not reversed when the direction of current flow is reversed are canceled out. Examples of such voltages are those due to thermoelectric and electrochemical effects. The total time of the current flow is sufficiently short so that heating effects in the sample do not significantly limit the accuracy of the measurement. However, a given direction of current flow is maintained for a sufficiently long period so that eddy currents do not significantly limit the accuracy of the measurement. The current can flow once in each direction; i.e., one reversal. For example, a current of +2 amperes flowing for 1 second can be followed by a current of −2 amperes flowing for 1 second. Alternately, the current can be reversed a multiplicity of times, so that the total charge (i.e., integrated current) flowing in each direction is equal. For example, a current of +2 amperes flowing for 0.5 second, −2 amperes for 1.0 second, and finally +2 amperes for 0.5 second. This latter sequence can in some cases provide for still improved accuracy, as when thermal potentials increase with time. The total current flow time is typically in the range of 0.05 to 10 seconds, and preferably in the range of 0.1 to 2 seconds. The cancellation of error potentials by the present technique allows currents of less than 10 amperes, and typically less than 5 amperes, to be utilized for the measurement.

Figure 2:
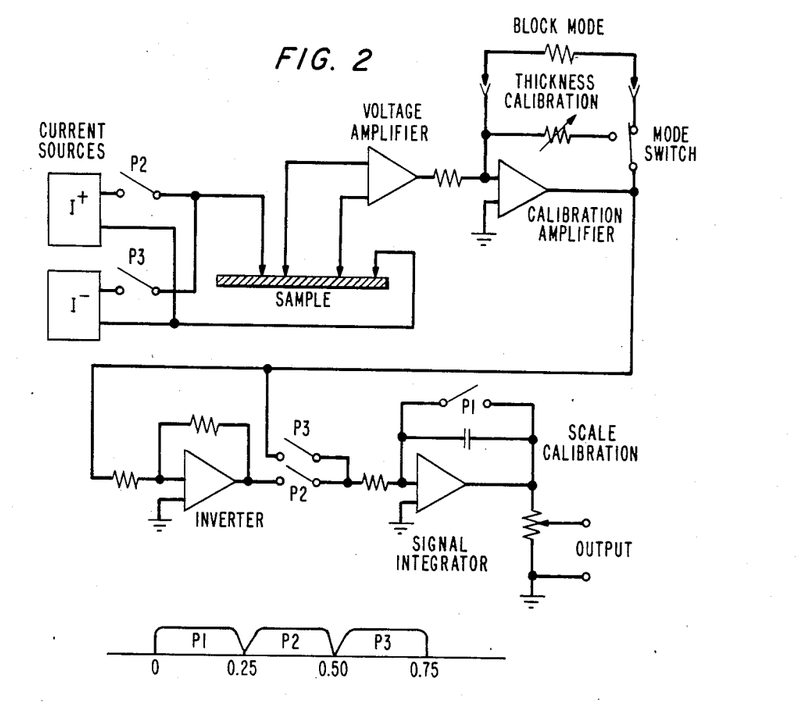
FIG. 2 shows a schematic diagram for implementing the present inventive technique.

FIG. 2 shows a block diagram of an exemplary circuit that accomplishes this, along with sequential time periods P1–P3. On command from a pushbutton control, a series of timing circuits zeroes the integrator during the first time period P1, turns the positive current (I+) on and connects the inverted amplified voltage signal to the input of the signal integrator during the second time period P2, and turns the negative current source (I−) on and routes the amplified signal directly to the integrator during the third time period P3. Each of these periods is typically about 0.25 seconds long. The signal integrator output can be read by a standard digital voltmeter; for a portable instrument, a liquid crystal display is desirable. The signal integrator provides a convenient means of combining the positive and negative signal voltages and of averaging out noise and other rapidly varying stray voltages. Since the voltage signal is inverted when the current flow is reversed, the integrator in effect combines the absolute value (i.e., magnitude) of the integrated voltages obtained for P2 and P3. It also retains the final measurement value.

In the circuit shown, the conversion between voltage measured across the probes and resistivity is made in the instrument. Since this conversion depends on sample thickness, the circuit must "know" the sample thickness, w. This information is supplied to the circuit by manually setting the "Thickness Calibration" potentiometer, which can conveniently be labeled directly in micrometers, millimeters, or mils. The effect of this potentiometer is to make the overall circuit gain inversely proportional to sample thickness so that the w on the right-hand side of Equation (1) is canceled by a 1/w term.

Figure 6:
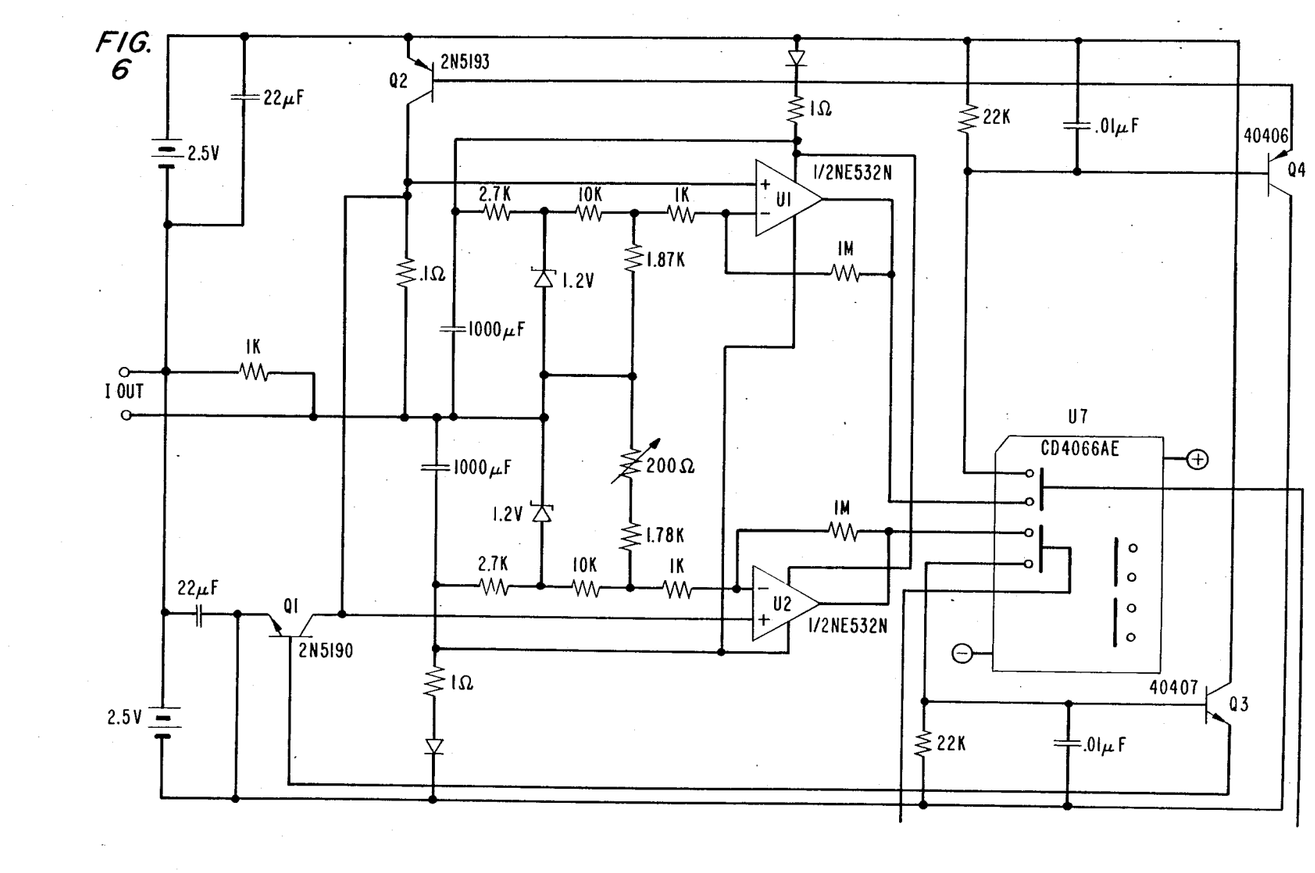
Figure 7:
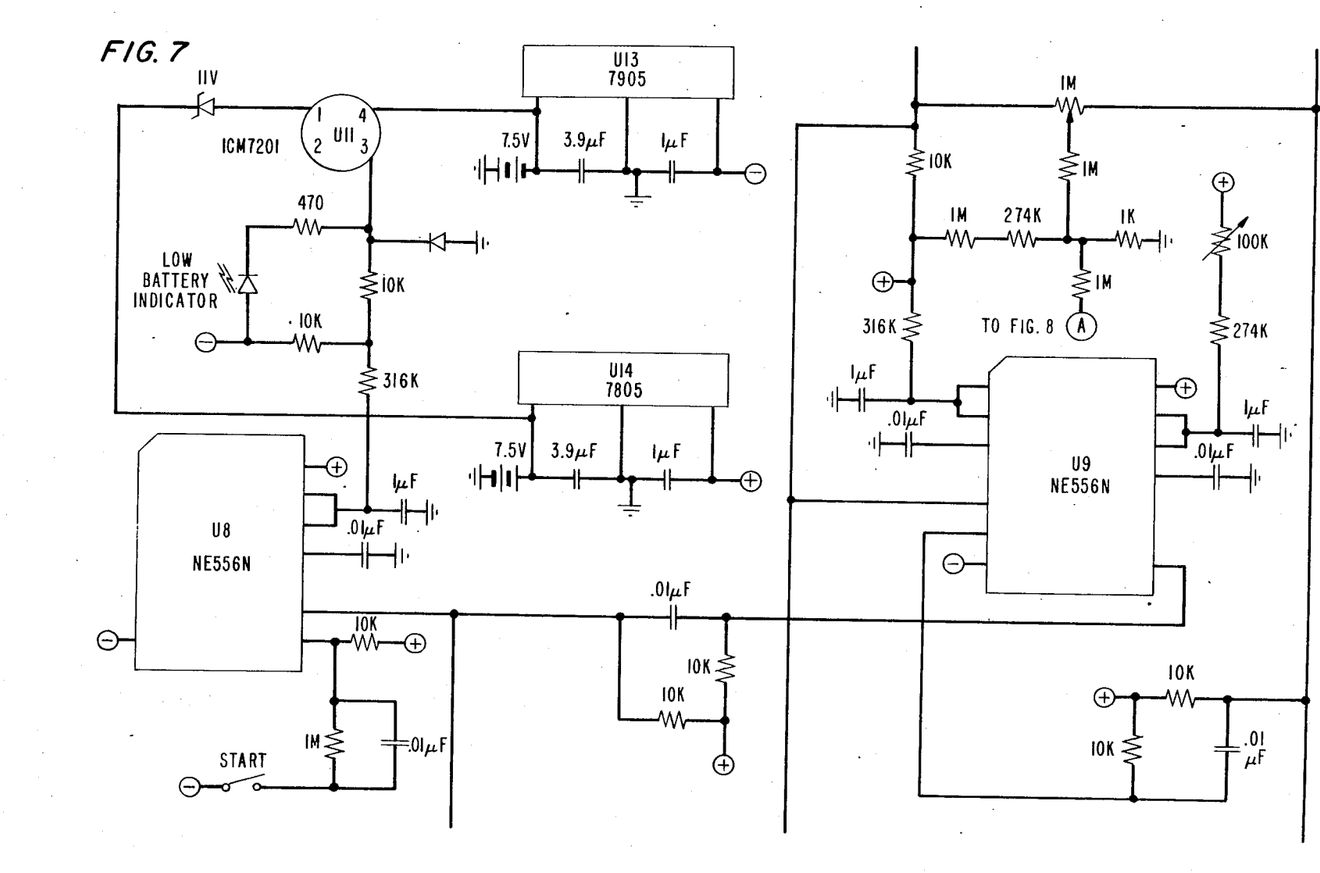
Figure 8:
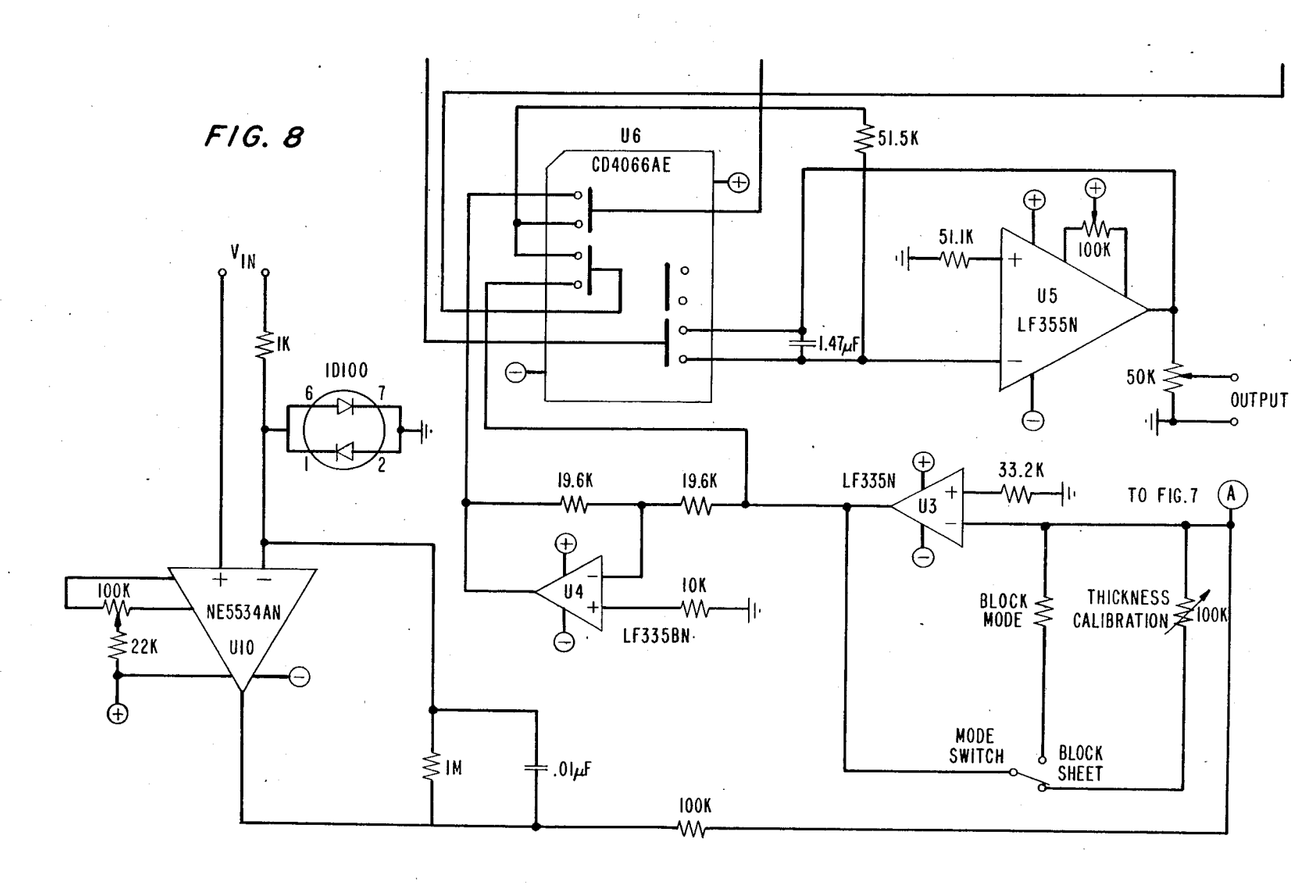

FIGS. 6–8 show in more detail a suitable circuit and component values. The design is isolated into blocks that are easy to understand; FIG. 6 generally describes the current sources and related switching circuit; FIG. 7 generally describes the power supply and timing circuits; and FIG. 8 generally describes the inverter, voltage integrator, and related switches. It will be apparent to those of skill in the art that numerous other implementations of the present invention are possible.

Referring to FIG. 6, the switched bipolar current sources used for providing current through the current probes comprise two complementary current regulators, with current being supplied by two pairs of 4 ampere-hour nickel-cadmium storage batteries. The junction between the two batteries floats. The 0.1 ohm precision resistor measures the current, and the voltage developed across it is compared with potentials derived from precision reference diodes. Regulated currents of about 2 amperes are easily obtained and provide adequate sensitivity. The two current sources (I+ and I−) are "floating" so that the common mode signal at the input of the voltage amplifier (U10 in FIG. 8) is considerably reduced. The positive and negative currents should be adjusted to be the same, within about 1-2%, by adjusting the potentiometer at the input of U2. U1 and U2 drive the output transistors, Q2 and Q1, through Q4 and Q3. The switches in U7 turn the current sources on only for the period of the measurement (P2, P3) so that actual battery drain is very low. Published battery ratings imply at least 4000 measurements on a single charge. The current drain on the ±5 volt lines is about 40 ma. The circuit shown utilizes COS/MOS switches, U6 and U7, which provide about 100 ohm resistance when closed and greater than $10^{12}$ ohm resistance to the control line and ground when open. They take the outputs of the timing chain (U8 and U9) and use them to switch circuits in the signal path and the measuring current path.

Referring to FIG. 7, the 5 volt power is supplied by 5 volt regulators (U13, U14) on 7.5 volt batteries; U11 provides an indication of battery condition. A reduction in battery drain can be achieved by the use of low-current operational amplifier and timing modules. The timing signals are obtained from integrated circuits U8 and U9, which provide three univibrators in sequence. During P1, the 1.47 microfarad integrator capacitor at U5 (FIG. 8) is discharged, and this timing is relatively unimportant. The actual times of P2 and P3 are likewise relatively unimportant, but they determine the time for which the signal is integrated, and so should be stable. The duration of P2 should be adjusted to be within about 0.2% of that of P3 to cancel out thermal emf's and input offsets in U10. The 1 megaohm potentiometer associated with U9 is adjusted to null out stray voltages induced by the current pulses that appear at the input of U3 (FIG. 8).

Referring to FIG. 8, the voltage amplifier U10 is a low noise type that provides a voltage gain of about 1000. This is followed by the "calibration amplifier" U3. The circuit can operate either in a "block" mode when measuring relatively thick samples (w > 3s) or a "sheet" mode for relatively thin samples (w < 0.5s). The mode in use is determined by which thickness calibrating resistor is selected. In the sheet mode, the "thickness calibration" potentiometer is adjusted by the user to set the system gain to adjust for sample thickness. In the block mode, the gain is set by a fixed resistor, typically mounted in the changeable probe assembly. The value of the "block mode" resistor (R) in kilohms is R = 1.39s, where s is the probe spacing in mils (0.001 inch). The inverting amplifier U4 and integrator U5 are straightforward. U5 has been chosen to be a low-input-offset type to keep the integrator output potential from drifting after the measurement. The 100 kilohm balance potentiometer at U5 compensates for input offsets in U4 and U5.

The overall calibration is set by the 50 kilohm output divider. The preferred way to set the calibration is by using the instrument to measure a sample sheet of known high resistivity, and then setting the calibrating potentiometer to make the output correspond thereto. It is unwise to depend on tabulated resistivity values to establish the calibration. If a sample of known resistivity is not available, a test sample of precise dimensions can be cut from a sheet and its resistance measured with a standard 4 lead technique. The resistivity can then be determined from $\rho = RA/l$, where R is the measured resistance, A is the cross-sectional area, and l is the sample length. (The difficulties of doing this make the value of the present technique even more evident.) With the component values shown in FIGS. 6-8, an output meter with 2 V range and 10 mV least count reads resistivity directly in microhm-cm, with a least count of 0.1 microhm-cm. This range nicely covers the steel resistivities normally encountered, about 9.8 microhm-cm for pure iron, 12-15 microhm-cm for low-carbon steels, about 50 microhm-cm for Si alloy transformer steels, and about 70 microhm-cm for 304 stainless steel.

Figure 3:
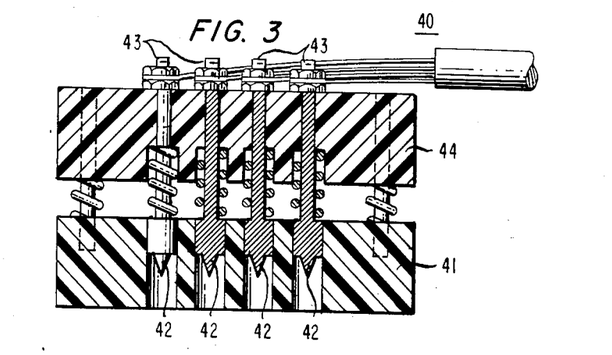
FIGS. 3–4 show a retractable 4-point probe suitable for use with the present technique.
Figure 4:
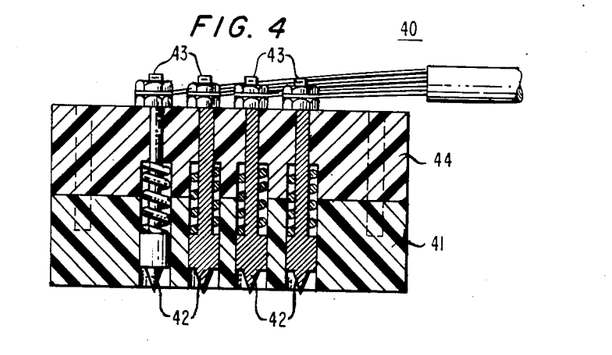
Figure 5:
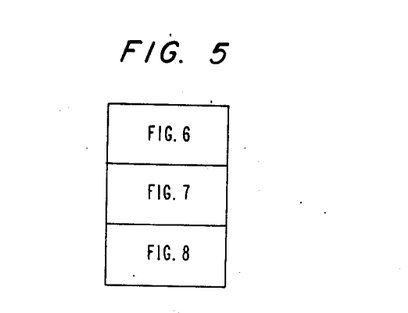
FIGS. 5–8 show schematically a circuit suitable for implementing the present technique.

A variety of 4-point probe arrangements is possible, including prior art type probes used for semiconductor measurements. A presently preferred design is shown in FIGS. 3-4, where the probes are protected by a spring-loaded plate 41 when not pressed against a sample. The probes have four identical spring-loaded points 42, individually pressed against the surface to be measured with a force equivalent to that exerted by a 1 kg mass. The spring constants and the gap between blocks 41 and 44 are selected so that only after block 41 is pressed against the article to be measured do the contact points (42) contact the article; see FIG. 4. In addition, the holes shown in block 41 provide a close fit and precise location for points 42. This arrangement prevents lateral motion of tips 42 as applied to the surface to be measured, and helps ensure high accuracy of the measurement. Precise spacing of the probe points is achieved by using brass rods 43 sliding in holes in a 1 inch thick phenolic laminate block 44. To provide for variable spacing of the probes, spacer inserts can be provided between the probes. The contact points are tungsten-carbide needles having a tip radius of 0.002 inch, held in the brass rods by setscrews; osmium-plated steel or other hard material can be used for the tips. This combination of point material and spring force is typically chosen to make measurements through even thin paint layers. The probes are connected to the measuring circuit by a 3 foot long cable of shielded No. 18 wire.

The design of the circuit and the precision of the components used provide an accuracy of typically better than ±5% for resistivity measurements. The accuracy is typically about ±1% when precise calibration has been made. Repeated measurements on the same piece of steel show scatter of about the least count, typically ±0.1 microhm-cm, even for high-resistivity alloys. The week-to-week reproducibility appears to be well within ±1%. Thin layers of rust, oil, or paint do not appear to affect the indicated resistivity significantly. In addition, electroplated objects have been successfully measured; for example, the resistivity of a tool steel substrate metal having a chrome plating has been accurately indicated. For sheets thinner than about 0.03 inch, the greatest source of uncertainty is the accuracy with which the thickness can be determined. A 1% error in the thickness (measured, e.g., with a micrometer), corresponding to only 0.3 mil, will produce a 1% error in the apparent resistivity. Surface texturing may make the apparent thickness of the sheet greater than that of the effective thickness, resulting in an erroneously large measured resistivity. We estimate that the temperature coefficient of the calibration is significantly less than the temperature coefficient of steel, which is about 0.3–0.5%/°C.

The present technique is of sufficient precision for checking sample or lot variations in the resistivity of sheet steels. This can provide, for example, matched alloys to obtain reproducible weld penetrations. However, the ease and rapidity of the measurement make possible many additional applications to ferrous and nonferrous metallurgy. Some examples are given below. Although low-carbon, low-alloy steels have resistivities which substantially depend only on composition, more complex steels have a large variation in resistivity with heat treatment, resulting, for example, from the austenitic-martensitic transition. Direct resistivity measurements provide an easy means of testing for the completeness of the transformation.

The resistivity of silicon transformer steels is an important parameter because of its relationship to eddy current losses. The present technique can measure the resistivity without cutting special test coupons. In fact, resistivity can be measured in the presence of the heavy oxide layer normally present on these steels—there is no need to sand off the oxide. The resistivities of commercial magnetic alloys (Permalloy, etc.) vary over a wide range. These materials can be easily sorted and distinguished by resistivity measurements. Many magnetic stainless steels, which have similar appearance, can be distinguished. Additionally, there are some nominally nonmagnetic materials which may have significant susceptibility. Obvious examples are the "nonmagnetic" stainless steels, and materials such as Cu-Ni-Sn spring material, which may have magnetic impurities or be magnetic if improperly processed. For these alloys, the present technique is an improvement over typical eddy current methods of determining resistivity.

The pressure of the probe tips substantially punches through the native oxide layers on the surface of the metal. Only very small emf's (a few hundred microvolts) are typically developed at the probe tips, which voltages are inadequate by themselves to break down the native oxide layer present on most metals. Therefore, if the metal is formed of several layers, the native oxide between the layers substantially constrains the current flow from the probe to be within the top layer. For example, the resistivity of a tightly rolled coil of sheet can be measured without opening the coil.

The following Examples illustrate a variety of measurement situations that can advantageously utilize the present technique.

EXAMPLE I

Table I shows results of measurements on a number of materials we have studied. As noted above, for thin samples, the accuracy with which the thickness determination can be made is the main limit on the absolute accuracy obtained. In many cases, differences between the measured resistivity and handbook values arise from variations in the exact alloy composition or the cold work/thermal history of the sample. It is important that these deviations are seen, since they are signs of the variables that are desirable to observe for quality control purposes.

TABLE I

Room temperature resistivity values measured on various materials with the instrumentation described here (thicknesses in mils, resistivities in microhm-cm).

| Alloy | State | 4-Point Probe Measurement | Conventional Measurement | Handbook Value |
|---|---|---|---|---|
| Fe—5% Cr | 55.5 thick | 32.1 | 30 | |
| Permalloy | 53 thick | 64.7 | 65 | |
| Fe—5% Cr—3% Si 52 thick | cold rolled annealed | 68.8 66.9 | | ~72 |
| Fe—3% Si Steel | 13.5 thick | 48.6 | | ~47 |
| CDA 194 alloy Cu—97% Fe—2.4% 10 thick | different samples | 4.0 2.6 2.6 | | 2.65 |
| CDA 195 alloy Cu—97% Fe—1.5% Sn—0.6% 10 thick | different samples | 3.4 3.5 3.6 3.8 | | 3.4 |

EXAMPLE II

The utility of resistivity measurements in characterizing metals obviously depends on whether materials have different resistivity values, either from compositional variations or from phase changes. Table II shows published resistivity values for some commercial alloys taken by prior art methods. Clearly, the wide range of values observed suggests that the present technique is useful for sorting and materials certification. For low-alloy steels, there is a well-established relationship between the composition and the resistivity. Resistivity is also directly correlated with weld penetration in low-carbon steels (see below). For the copper alloys, where electrical conductivity is important, the 4-point probe technique allows direct determination of this property for each batch of material. Although handbook values of the resistivity are often assumed, different temper and anneal conditions can lead to variations of more than a factor of 2 in the resistivity of copper base alloys.

TABLE II

Resistivity values for various commercial alloys.

| Family | Material | Room Temperature Resistivity, microhm-cm (typical) |
|---|---|---|
| Ferrous | Iron | 9.8 |
| | 1010 Steel | 13 |
| | 4130 Steel | 22 |
| | 304 SS | 75 |
| | 410 SS | 56 |
| Copper base | Copper | 1.7 |
| | Phos. Bronze (1% Sn) | 3.6 |
| | Be-Cu (2% Be) | 7.7 |
| | CDA 194 (2% Fe) | 2.5 |
| | Bronze (5% Al) | 10 |
| | Yellow Brass (No. 270) | 6.4 |
| Aluminum | Aluminum | 2.8 |
| | 2024 | 5.7 |
| | 5052 | 4.9 |
| Titanium | Titanium | 48.2 |
| | 315 (2% Al 2% Mn) | 101 |
| | 318 (6% Al 4% V) | 168 |
| Superalloys | Inconel X | 122 |
| | Hastelloy C | 139 |
| | Stellite 25 | 88 |
| | Monel K | 58 |

EXAMPLE III

Table III shows the resistivity changes that can arise from heat treatment (and the consequent precipitation and recrystallization) of various alloys. The values shown are published values taken by prior art techniques. In many cases, these changes are large enough to use for quality control purposes to determine, for example, whether heat treatment has led to the desired phase. An important advantage of the resistivity measurements over many competing techniques is that a significant volume of the sample is measured (i.e., to a depth of about the probe spacing), rather than just the surface. This distinction can be important in view of the effects of surface oxidation, segregation, and cold work in making the surface different from the bulk.

TABLE III

Some alloys which show large variation of resistivity with anneal or cold work.

| Alloy | Condition | Room Temperature Resistivity (microhm-cm) |
|---|---|---|
| Fe—30% Ni | Ferritic | 38 |
| | Austenitic | 83 |
| 2014-T6 Aluminum | 70 kpsi yield | 4.5 |
| | 28 kpsi yield | 3.4 |
| Cu-2% Be | soft anneal | 9.4 |
| (CDA 172) | heat treated | 7.1 |

One item in Table III is of such significance that it is worth emphazing. That is the large resistivity change occurring in phase transformation in iron alloys. In most cases, the resistivity decreases by a factor of 2 or more on the transition into the body centered cubic or martensitic phase. This phenomenon has been widely used in laboratory studies of the martensitic transformation. The development of the 4-point probe technique we describe here makes it possible to use this change to measure directly the state of transformation of massive objects in their finished or semi-finished state. The present technique provides measurements on the bulk of the material, not simply a thin surface layer.

We have so far implicitly assumed that the material being studied was homogeneous. Inhomogeneities such as voids, cracks, and slag and flux inclusions are in general nonconductive and sharply raise the observed resistivity if they are in the vicinity of the voltage probes. We estimate that voids 0.1s in diameter can be detected if they are within a distance s of the surface. Cracks perpendicular to the surface and the line made by the probe points can be observed if the crack length×depth is about $0.1s^2$. Cracks perpendicular to the surface but along the line of the probes have a much smaller effect. This difference allows localization and measurement of the size of defects. For a review of the determination of crack size by resistivity measurements, see "The d.c. Electrical Potential Method for Crack Length Measurement," by M. J. Halliday et al, in *The Measurement Of Crack Length And Shape During Fracture And Fatigue*, C. J. Beevers, Ed., pages 85–112, Engineering Materials Advisory Services, Ltd., Wanley, U.K. (1980).

Figure 9:
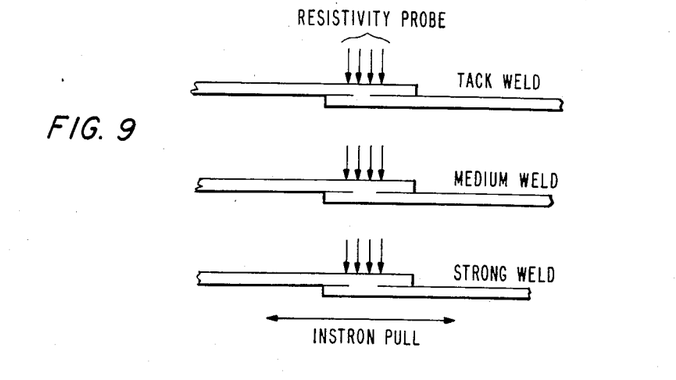
FIG. 9 shows the inventive technique measuring the strength of welds.
Figure 10:
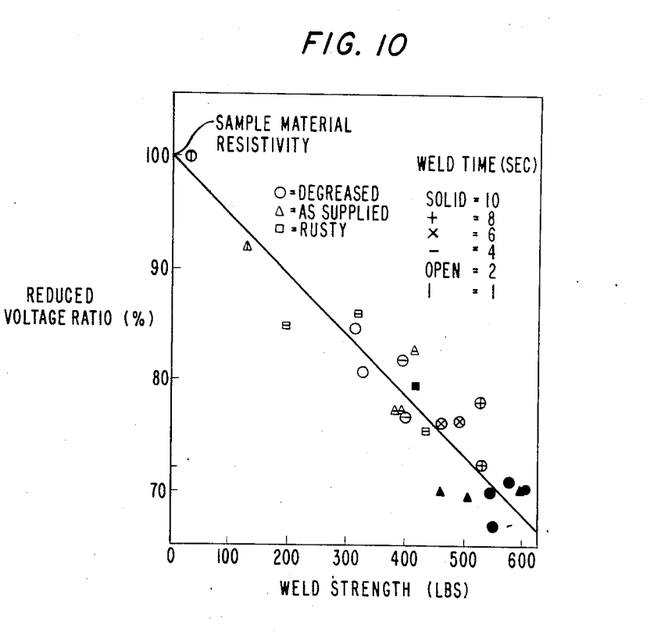
FIG. 10 shows an empirical relationship between weld strength and the reduced voltage ratio measured by the inventive technique.
Figure 11:
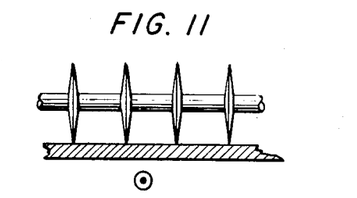
FIGS. 11–14 show probes suitable for performing measurement on moving specimens.
Figure 12:
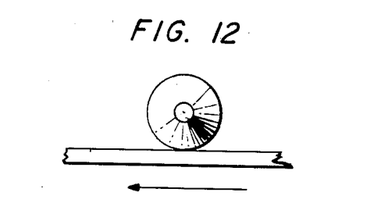
Figure 13:
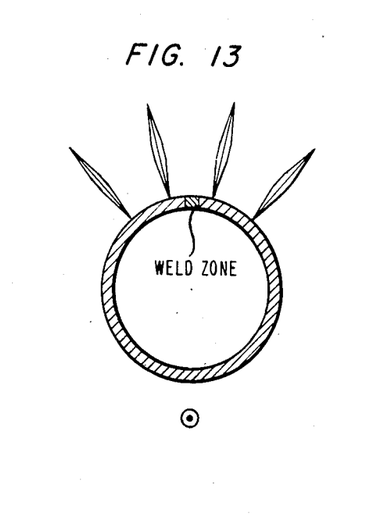
Figure 14:
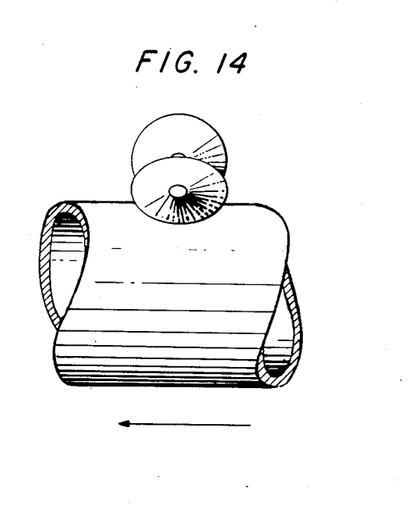

The present technique can also provide a direct correlation between the electrical measurements and the ultimate weld strength for spot welds. FIGS. 9–10 show how this process works. The 4-point probe puts a current through the metal sheet using the two outer probe tips. The current produces a voltage drop through the sample, and the voltage drop is measured by the inner pair of probe tips. The equations relating the probe spacing, material dimensions, current, voltage, and resistivity have been solved by Uhlir; see "The Potentials of Infinite Systems of Sources and Numerical Solutions of Problems in Semiconductor Engineering," A. Uhlir, Jr., *The Bell System Technical Journal*, Vol. 34, pages 105–128 (1955). For a given test current and material resistivity, the voltage across the inner probe tips is decreased when a weld has been made, because the lower sheet of metal helps to conduct the current where the two sheets are bonded together.

Analysis of a simplified case shows what effects can be expected: for the case where the probe spacing, s, is very much smaller than the sheet thickness, w, the voltage drop across the inner probes is (see Equation (1) above):

$$V = I\rho/4.53\,w \qquad (3)$$

with I the current through the outer probes and $\rho$ the material resistivity in ohm-cm (w is in cm). If the weld is large compared to the overall probe span, the probe sees the equivalent of a single sheet of metal of thickness 2w, and the observed voltage decreases to half of that measured before the weld, assuming the upper and lower sheets to be of the same material and thickness. Obviously, the effect on the measured voltage is even larger if the upper sheet is thinner than the lower, and vice versa.

For realistic situations, the weld fusion diameter, sample thickness, and probe spacing are all in the same range, and the simple Equation (3) is only a rough guide. An analytic solution for V in the geometry shown in FIG. 9 is probably not possible; the problem can be solved by finite element methods using the advanced codes now available, but the analysis is complex. However, a simplified method illustrates the relationship between the electrical measurements and weld strength. First, the voltage (VF) is measured across the voltage probes for the unwelded sheet. Then, the voltage (VN) is measured across the probes in the vicinity of the weld. The ratio VN/VF starts at 100% for negligible weld zone and (in the simplified case) decreases to 50% for fusion between the sheets all along the interface. For realistic cases, the behavior is more complicated, but one can establish at least an approximate relationship between the weld strength and the voltage reduction VN/VF, using this ratio as an indication of the extent of the fusion zone. The voltage developed in the sample is typically only 100 microvolts, and this is inadequate to break down the oxide layer between the sheets. Thus, only in regions where fusion between the two sheets has been obtained will significant current flow occur.

EXAMPLE IV

Single spot weld lap joints were made in 1 inch×4 inch SAE 1010 steel pieces, with samples 0.030 inch thick welded by resistance spot weld. For the 0.030 inch samples, copper electrodes of 0.125 inch tip diameter were used, with a contact force of 30 pounds, a weld current of 2500 amperes, and weld times of 1–10 cycles (0.017–0.17 second).

Three surface conditions were used for the resistance spot welds: as received (covered with a light oil film), degreased, and "rusty". The surfaces were made rusty by exposing the steel to boiling salt water for a few hours until the surface was covered with a thick but adherent oxide layer. Welds were made with one rusty surface and one clean surface, and two rusty surfaces. After the welds were made, the voltage reduction ratio was measured using the instrumentation previously described, with 0.062 inch probe spacing. The probe was aligned by eye to have the 4 points centered on the visible electrode spot. Measurements were made on both the top and bottom of the spot-welded joints, and were in all cases the same within the 2–3% reproducibility of the measurements. After the voltages were measured, the samples were pull tested on an Instron tensile tester at a rate of 0.5 inch/minute, and the maximum force was read from from a strip chart. Except for the weakest welds, failure was by pull-out of the weld nugget; i.e., ductile failure of the steel at the edge of the fusion zone.

FIG. 10 shows the weld strength versus voltage reduction ratio for all of the resistance spot welds tested. The data show that the voltage reduction ratio is an excellent indicator of the actual weld strength. For all of the welds tested, the actual strength was within 100 pounds of the trend line in FIG. 2, or less than 20% of the maximum weld strength. This accuracy was obtained over a 10:1 range of weld energy and despite gross intentional contamination of the surfaces to be welded.

The test described herein for weld strength depends on using the electrical conductivity of the workpieces to estimate the size of the fusion zone and, therefore, the weld strength. There are two principal limitations on the generality of this test. First, if the material is embrittled or otherwise weakened by the welding operation, i.e., by recrystallization into a brittle phase, a large fusion zone, and thus a large conductivity change, would be produced, but the weld could nevertheless be susceptible to brittle failure at very low forces. Second, as noted above, there are many alloys which change resistivity significantly when they are heated and quenched. For these materials, the inherent change of resistivity could mask the changes resulting from the formation of the weld. In such cases, however, study of test samples should reveal a range of reduced voltage ratio which is characteristic of good welds. Fortunately, low-carbon steels and soft aluminum, two of the most commonly spot-welded materials, are largely unaffected by these restrictions.

Although only individual isolated welds were measured above, frequently a row of spot welds is produced. Calculations by Smits (above) allow us to estimate that for spacing between welds of greater than 3 times the distance between the outermost probe points, the voltage reduction ratio will not be significantly affected. For closely traced spot welds or seam welds, additional corrections and calibrations can be made.

The close relationship between electrical and thermal conductivity in the metals makes it possible to use the present technique for determining the thermal conductivity of metallic samples. The relationship between the two conductivities is described by the law of Wiedemann-Franz (see C. Kittel, *Introduction To Solid State Physics*, Wiley, New York, Second Edition, 1956, page 241). Experimental verification of this effect, and indication of its utility in practical cases, appear in "Nominal Mechanical and Physical Properties of Commercial Heat-Treatable Copper Alloys at Room Temperature," in *Handbook Of Materials And Techniques For Vacuum Devices*, W. H. Kohl, Reinhold Publishing Company, New York (1967). This table shows that the ratio (thermal cond/electrical cond) is constant within ±10% for a wide range of copper base alloys and heat treatments. The range of thermal conductivities is approximately 5:1.

While an in-line 4-point probe has been described above, other implementations of the probe are possible. For example, crossed 4-point probes can be utilized for better estimating the weld strength between metals when the weld is not of a circular geometry. To provide for a continuous measurement of resistivity, the probes can be in the form of rollers, as illustrated in FIGS. 11–14 for measuring either flat or curved moving articles. It is also possible to place probes on opposite sides of a piece of metal. The current flow can then be through the thickness of the metal. For example, the use of a multiplicity of electrodes on opposite surfaces of a weld is described in European Patent Application No. 0,030,889, filed Dec. 8, 1980. Numerous other configurations and utilizations are possible, as will become apparent to a person of skill in the art.

What is claimed is:

1. A method of testing an article characterized by contacting metal having a volume resistivity of less than 200 microhm-cm by means of at least four spaced probes;
    passing a current in a first direction between two of said probes and integrating the voltage produced thereby across another two of said probes;
    thereafter reversing said current while again integrating said voltage produced thereby; and
    combining the magnitudes of the integrated voltages;
    wherein the duration of the flow of said current is in the range of 0.1 to 2 seconds and wherein said reversing of said current is performed once per test.

2. The method of claim 1 wherein all of said probes contact the same surface of said metal.

3. The method of claim 1 wherein at least two of said probes contact a first surface of said metal, and at least another two of said probes contact an opposite surface of said metal.

4. The method of claim 1 wherein said current is less than 10 amperes.

5. The method of claim 1 wherein said metal is a magnetic metal having a magnetic permeability of greater than 1.05.

6. The method of claim 1 wherein said metal is a nonmagnetic metal having a magnetic permeability of less than 1.05.

7. The method of claim 1 wherein a resistivity value is obtained from the combined integrated voltages that is within 5% of the actual resistivity value of said metal.

8. The method of claim 1 wherein said probes are placed in the vicinity of a weld in said metal, whereby at least a portion of said current flows through at least a portion of said weld, thereby obtaining a measurement of the strength of said weld.

9. The method of claim 1 wherein the total time of said passing a current is sufficiently short so that heating effects in said metal do not substantially limit the accuracy of said testing, and wherein the time of said passing a current in a given direction is sufficiently long so that eddy currents in said metal do not substantially limit the accuracy of said testing.

10. An apparatus for testing an article characterized by means for contacting a metallic portion of said article with at least four probes;

means for causing a current to flow in a first direction between two of said probes for a first time period;

means for causing a current to flow in the opposite direction between said two probes for a second time period;

means for integrating the voltages produced by said currents across another two of said probes; and means for combining the magnitudes of the integrated voltages;

wherein said apparatus is adapted for testing a metallic portion having a volume resistivity of less than 200 microhm-cm, and adapted to flow said current once in each direction per test, with the total duration of the flows being in the range of from 0.1 to 2 seconds per test.

11. The apparatus of claim 10 wherein said apparatus provides a resistivity measurement of said metallic portion that is accurate to within ±5% of the actual volume resistivity of said portion.

12. The apparatus of claim 10 wherein said apparatus is adapted for testing a weld, whereby the combined integrated voltages provide a measurement of approximate weld strength.

13. The apparatus of claim 10 wherein said current is less than 10 amperes.

14. The apparatus of claim 10 wherein said means for causing a current to flow in said first direction and said second direction provide for a total time of current flow that is sufficiently short so that heating effects in said metallic portion do not substantially limit the accuracy of said testing, and provide for a time of current flow in a given direction to be sufficiently long so that eddy currents in said metallic portion do not substantially limit the accuracy of said testing.

15. A method of testing an article
characterized by
contacting a metal substantially comprising iron and having a volume resistivity of less than 200 microhm-cm by means of at least four spaced probes;

passing a current in a first direction between two of said probes and integrating the voltage produced thereby across another two of said probes;

thereafter reversing the direction of said current and integrating the voltage produced thereby;

and combining the magnitudes of the integrated voltages;

wherein the total time of the passing of the current is sufficiently short so that heating effects in said metal do not substantially limit the accuracy of said testing, and wherein the time of the passing of the current in a given direction is sufficiently long so that eddy currents in said metal do not substantially limit the accuracy of said testing.

16. The method of claim 15 wherein said testing provides a resistivity measurement of said metal that is accurate to within ±5 percent of the actual volume resistivity of said metal.

17. The method of claim 15 wherein the current is less than 10 amperes.

18. The method of claim 15 wherein the current is passed only once in each direction per test.

19. The method of claim 18 wherein the total time of passing the current is less than 2 seconds.

20. The method of claim 19 wherein the total time of passing the current is at least 0.05 seconds.

21. The method of claim 15 wherein said metal is a magnetic metal having a magnetic permeability of greater than 1.05.

* * * * *